United States Patent [19]

Kordes

[11] Plant 4,658

[45] Mar. 3, 1981

[54] ROSE PLANT

[75] Inventor: Reimer Kordes, Aspern, Fed. Rep. of Germany

[73] Assignee: Armstrong Nurseries, Inc., Ontario, Calif.

[21] Appl. No.: 80,381

[22] Filed: Oct. 1, 1979

[51] Int. Cl.[3] ..... A01H 5/00
[52] U.S. Cl. ..... Plt./11
[58] Field of Search ..... Plt./11

*Primary Examiner*—Robert E. Bagwill
*Assistant Examiner*—James R. Feyrer
*Attorney, Agent, or Firm*—William H. Elliott, Jr.; Andrew R. Klein

[57] ABSTRACT

A Hybrid Tea rose, of half-hardy character, being an outdoor seedling for garden decoration. The plant is of bushy, upright and vigorous growth habit, and much-branched. It is of medium height for roses of the Tea class. Flowers are generally borne singly, ranging from 13 to 15 cm. in diameter. They are, at first opening, a very light pink or a very pale apricot, becoming basically cream-colored, turning to off-white in about three days. Blooms have moderate to strong spicy fragrance. Mildew resistance is above average compared to plants grown under similar conditions.

1 Drawing Figure

This invention relates to a new variety of Hybrid Tea rose. The plant is a bushy outdoor seedling of medium height, grown mainly for garden decoration. It was asexually reproduced by Reimer Kordes in Sparrieshoop, Holstein, West Germany, having as its seed parent "Colour Wonder" and for pollen parent "King's Ransom." The plants described herein were grown in Ontario, Calif., from budwood of the new variety. The variety is classed as half-hardy, according to tests conducted by All-American Rose Selections, Inc. The new variety holds its distinguishing characteristics through succeeding propagations by budding.

The plant bears its flowers mostly singly, on normal to strong stems of medium length. It flowers freely, and almost continuously throughout the growing season. The blooms have a moderate to strong spicy fragrance.

Among the ways in which the new rose may be distinguished from its seed parent, "Colour Wonder", are the following:

Flowers of the new rose are basically cream-colored as described below, but flowers of the seed parent are orange-coral with a cream reverse.

Flowers of the new cultivar have 28 to 34 petals, whereas "Colour Wonder" blooms contain about 50 petals.

"Colour Wonder" blooms are only slightly fragrant, while blooms of the new rose carry a moderate to strong spicy fragrance.

The plant of "Colour Wonder" has considerably more large and small prickles than the new cultivar.

In comparison with the pollen parent, "King's Ransom":

"King's Ransom" has generally 35 to 40 obovate petals, whereas the new rose has usually 28 to 34 nearly round to very broadly obovate petals.

"King's Ransom" blooms are clear golden yellow in coloration; blooms of the new rose are cream-colored.

Foliage of "King's Ransom" is considerably glossier than foliage of this new variety.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is of average length, average to heavy in caliper, and erect, with numerous stipitate glands and a few small prickles. The color is generally between Strong Yellow Green, 2.5GY6/8, and Moderate Yellow Green, 2.5GY5/5, sometimes overlaid with near Dark Red, 2.5R3/7.

Before the calyx breaks, the bud is of medium size, medium-length and pointed and ovoid in form, with foliaceous appendages and some stipitate glands on the surface of the bud. Usually, slender foliaceous parts extend beyond the tip of the bud equal to one-fourth or more of its length.

As the calyx breaks, the color is between Light Orange, 2.5YR8/6, and Deep Pink, 2.5R6/11. The inner surface of the sepals carries a fine tomentum. The margins are normal.

As the first petal opens, the bud is of average size, medium-length, pointed and ovoid in form. The color on the outside of the petal is between Strong Yellow Green, 2.5GY7/10, near the base and Strong Pink, 2.5R7/8, near the margins. The color of the inside surface of the petal is between Vivid Greenish Yellow, 7.5Y8/12, near the base, and Moderate Yellowish Pink, 7.5R8/6, in the outer half or more of the petal; generally with an irregular vegetative (greenish) streak running over the midrib. The bud opens up well and is not prevented from opening by cold, hot, wet, or dry weather.

BLOOM

The bloom when fully open is average in size, being from 13 cm. to 15 cm. in diameter. The petalage is double, with from 28 to 34 petals, plus from 1 to 3 petaloids arranged regularly. In form, the bloom is high centered at first, becoming flat to cupped to high centered. The petals remain at first somewhat tightly cupped with tips reflexed outward; later, at maturity, the petals become more loosely cupped, with tips reflexed outward.

The petals are of medium thickness, with inside slightly velvety and outside slightly shiny to satiny. The outside and intermediate petals are from nearly round to broadly obovate in form. The inside petals are broadly obovate to irregular. The colors may be modified by being blotched or tinted with other colors.

The following paragraphs describe color values observed in a flower newly opened in the month of September. The plant had been grown outdoors, in Ontario, Calif.

The color of the outside petal, both on its outer and inner surfaces, was between off-white and Pale Pink, 2.5R9/3.

The color of the intermediate petal, both on its outer and inner surfaces, was varying from off-white to Pale Pink, 2.5R9/3, to Pale Orange Yellow, 7.5YR9/4.

The color of the inside petal, both on its outer and inner surfaces, was between off-white and Light Orange, 2.5YR8/6.

The following paragraph describes the color values observed in a flower which had been open for three days, indoors, in the month of September. The plant had been grown outdoors in Ontario, Calif.

The color of the outside petal, both on its outer and inner surfaces, was off-white. The color of the inside petal, both on its outer and inner surfaces, was off-white with a very pale pinkish overcast.

The general color effect of the newly opened flower is creamy white to very pale pink to very pale apricot. After being three days open, the bloom gives a general color effect of off-white. The petals drop off cleanly, except for petaloids.

The flower on the bush in the garden persists for from 3 to 4 days in the month of September, in the locality named. Cut roses grown outdoors and kept at living-room temperatures will last from 3 to 4 days in the month of September.

REPRODUCTIVE ORGANS

The stamens are average in number and are arranged regularly about the pistils, a few being mixed with petaloids and/or tucked in the calyx.

The filaments are from medium-length to long and very pale yellow in color, sometimes overlaid with near Dark Red, 2.5R3/7. Most are with anthers.

The anthers are of medium size and all open approximately at once. Just after dehiscence, the coloration of the anthers is near Strong Yellowish Brown, 7.5YR5/7.

Pollen is moderate and near Strong Orange, 5YR7/11, in coloration.

The number of pistils is from an average number to many and, on the average, numbering approximately 125.

The styles are uneven, of average length to long, and their average caliper is heavy. They are loosely bunched and generally very pale yellow in color, overlaid beneath the stigma with near Dark Red, 2.5R3/7.

The coloration of the stigma is near Pale Orange Yellow, 7.5YR9/4.

Most of the ovaries protrude from the calyx.

Since this variety does not normally produce hips when grown outdoors in the locality named, there were no hips or seeds for description.

FOLIAGE

The compound leaves usually comprise from three to seven leaflets. They are from normal to abundant, of medium size, moderately heavy to somewhat leathery, and semi-glossy. The leaflets are ovate in form, with apex acute, base obtuse, and margin irregularly serrate.

On its upper surface, mature foliage is near Moderate Olive Green, 5GY4/3, in coloration. The under surface is near but grayer than Moderate Yellow Green, 5GY5/6.

Young foliage on its upper surface is a ground color near Strong Yellow Green, 5GY6/8, highly overlaid with near Dark Red, 2.5R3/7, covered with a light glandular bloom. The under surface has the same color values as the upper surface but without the glandular bloom.

The rachis is of average size, the upper side being grooved, with many stipitate glands on the edges. The under side is sparsely prickly and with a few stipitate glands.

The stipules are of medium length, from medium-width to wide, and with medium-length points turning out at an angle of usually less than 45°.

The plant displays a more than average resistance to mildew, when compared with other varieties now in commerce under comparable conditions, when grown at Ontario, Calif.

GROWTH

The plant is upright and bushy in habit and much branched, attaining a medium Hybrid Tea height. It displays a vigorous growth. Canes are of medium caliper.

The main stems have a coloration between Moderate Yellow Green, 2.5GY5/5, and Light Olive, 10Y5/5. They bear from several to many large prickles, which are medium-length, almost straight, and with moderately long, moderately broad base. Their color is between Strong Brown, 5YR4/5, and Brownish Orange, 5YR5/8. There are a few small prickles whose coloration is the same as the large prickles. There are no hairs.

The branches have a coloration which is between Moderate Yellow Green, 5GY5/6, and Moderate Olive Green, 5GY4/3. They bear from few to several medium-length large prickles which are from almost straight to hooked slightly downward, with medium-length moderately narrow base. These prickles are near Brilliant Greenish Yellow, 7.5Y9/8, in color. There are a few small prickles which are between Brownish Orange, 5YR5/8, and Strong Brown, 5YR4/5, in color. There are several stipitate glands, but no hairs.

New shoots have a ground coloration near Strong Yellow Green, 5GY6/8, moderately overlaid with near Dark Red, 2.5R3/7. There are a few large prickles and several small prickles being medium-length and almost straight. Both large and small prickles have a coloration which is near Moderate Red, 2.5R4/10, and somewhat translucent. There are several stipitate glands, but no hairs.

I claim:

1. A new variety of asexually reproduced Hybrid Tea rose plant of the outdoor bush type, substantially as herein shown and described, and being particularly characterized by the coloration of its blooms from light pink to pale apricot, to creamy white, said blooms having from 28 to 34 petals, plus 1 to 3 petaloids, and about 125 stigma, said blooms being usually borne one to a stem, and having a strong spicy fragrance.

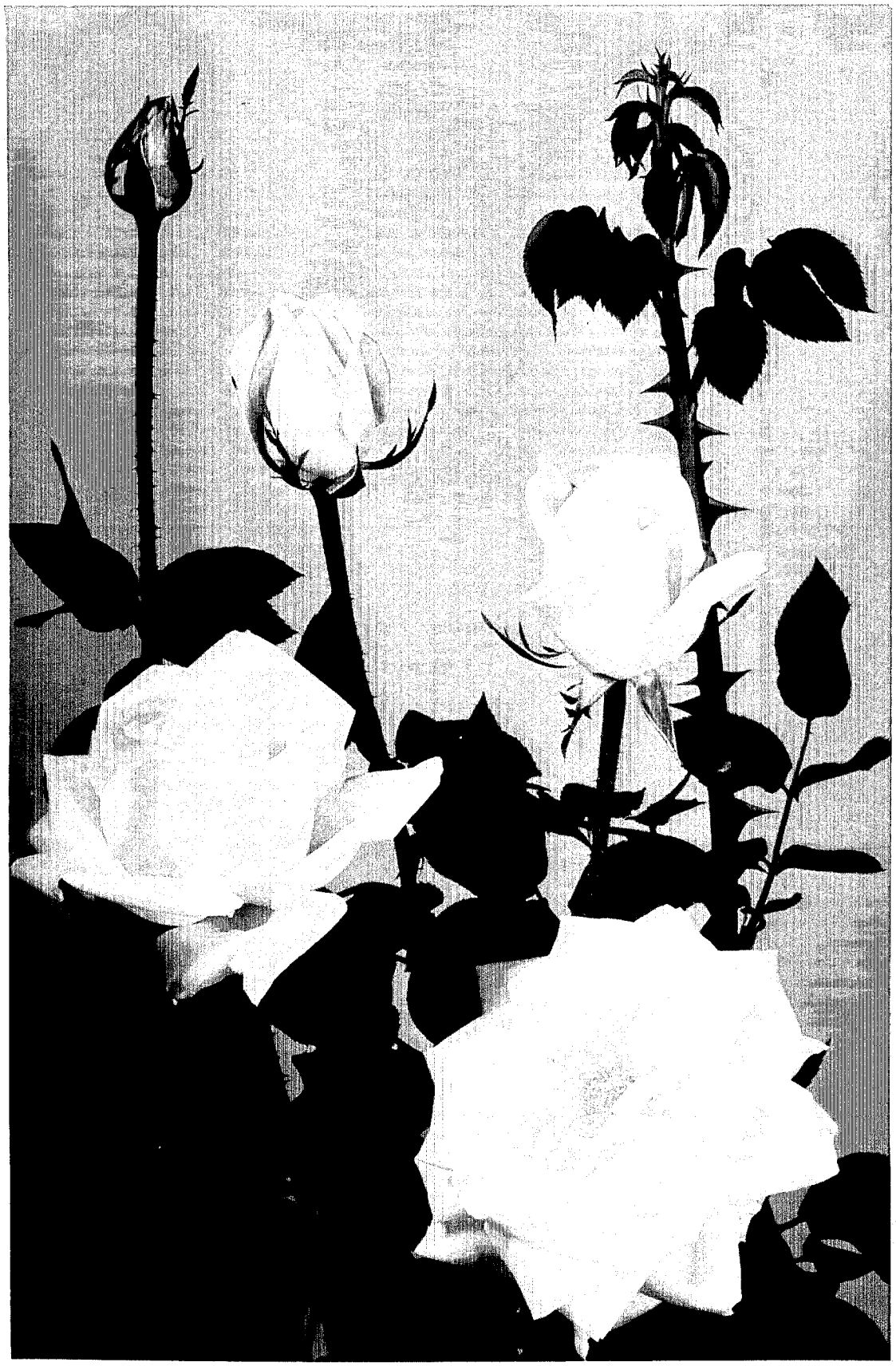

* * * * *